United States Patent [19]

Furumai et al.

[11] Patent Number: 5,374,552
[45] Date of Patent: Dec. 20, 1994

[54] PRODUCTION OF PRADIMICIN ANTIBIOTICS

[75] Inventors: Tamotsu Furumai, Yokohama; Masami Hatori, Yokosuka; Masatoshi Kakushima, Isehara; Chiharu Ikeda, Tokyo; Kyoichiro Saitoh, Zushi; Seikichi Kobaru, Chiba, all of Japan

[73] Assignee: Bristol-Myers Squibb Co., New York, N.Y.

[21] Appl. No.: 983,959

[22] Filed: Dec. 1, 1992

Related U.S. Application Data

[62] Division of Ser. No. 739,019, Jul. 31, 1991, Pat. No. 5,194,371.

[51] Int. Cl.$^5$ .................. C12N 1/12; C12P 19/56
[52] U.S. Cl. .................. 435/252.1; 435/78; 435/825

[58] Field of Search ............. 435/78, 252.1, 825

[56] References Cited

U.S. PATENT DOCUMENTS 5,053,395 10/1991 Nishio et al. .................. 514/33
5,091,418 2/1992 Sawada et al. ................ 552/201

OTHER PUBLICATIONS

*J. Antibiot.*, 1988, 41:807–811.

*Primary Examiner*—Herbert J. Lilling
*Attorney, Agent, or Firm*—Sandra M. Nolan

[57] ABSTRACT

The present invention relates to a fermentation process for producing BMY-28960 and desxylosyl BMY-28960, and to a novel BMY-28960-producing organism belonging to the genus Actinomadura and designated as strain AB 1236 (ATCC 55208).

1 Claim, 5 Drawing Sheets

PRODUCTION OF PRADIMICIN ANTIBIOTICS

CROSS REFERENCE TO RELATED APPLICATION

This application is a division of our co-pending application Ser. No. 07/739,019 filed Jul. 31, 1991 now U.S. Pat. No. 5,194,371.

BACKGROUND OF THE INVENTION

1. Field of the Invention

The present invention relates to a fermentation process for the production of pradimicin antibiotics, and to the producing microorganism of said antibiotics.

2. Background Art

Among the various reported members of the pradimicin family produced by Actinomadura, pradimicins FA-1 (Ia) and FA-2 (Ib), disclosed in U.S. Pat. No. 4,973,673, contain a D-serine moiety. Benanomicin A (II), a compound closely related to the pradimicins, has been reported in J. Antibiot., 1988, 41:807–811; it differs from the pradimicins in lacking the sugar amino group of the pradimicins. European Patent Application 432,527 published Jun. 19, 1991 discloses the compound 4'-deamino-4'-axial-hydroxypradimicin FA-2 (III, hereinafter referred to as BMY-28960) which was prepared from pradimicin FA-2 by chemical means. Desxylosyl BMY-28960 is also generically disclosed in EP 432,527 and may be prepared from desxylosyl pradimicin FA-2.

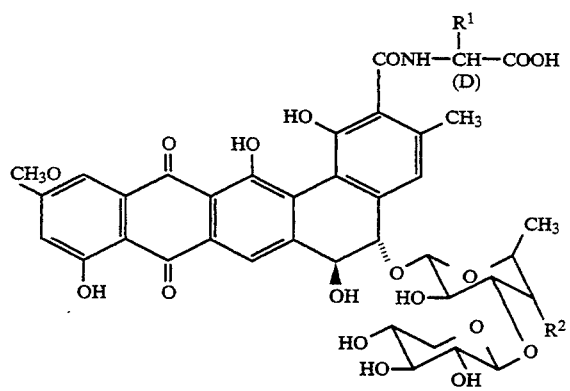

Ia: $R^1 = CH_2OH$; $R^2 = NHCH_3$
Ib: $R^1 = CH_2OH$; $R^2 = NH_2$
II: $R^1 = CH_3$; $R^2 = OH$
III: $R^1 = CH_2OH$; $R^2 = OH$

The chemical processes for preparing BMY-28960 and its desxylosyl derivative are difficult and laborious, and produce the products in low yield. Thus, an alternative process suitable for mass production of these antibiotics is highly desirable. As a result of an intensive search for microorganisms capable of producing BMY-28960 and desxylosyl BMY-28960, a novel microorganism strain belonging to the genus Actinomadura was found to be such an antibiotic producer.

SUMMARY OF THE INVENTION

The present invention provides a process for the preparation of an antibiotic of the formula

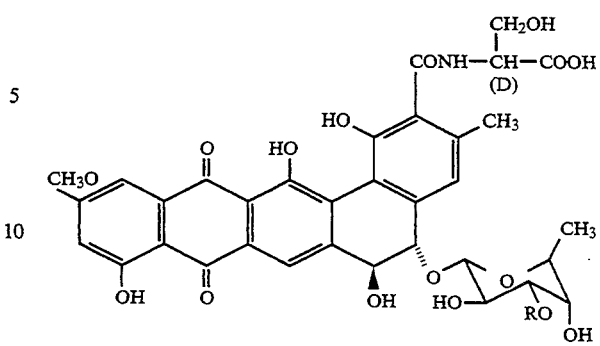

wherein R is hydrogen or β-D-xylosyl, which comprises cultivating a strain of Actinomadura capable of producing said antibiotic in an aqueous medium containing an assimilable source of carbon, nitrogen, and D-serine under aerobic conditions, and recovering said antibiotic from the cultured broth. Preferably the producing organism is Actinomadura sp. AB 1236, ATCC 55208. In a preferred embodiment, the fermentation medium further contains D-cycloserine.

In another aspect the present invention provides a biologically pure culture of the microorganism Actinomadura sp. AB 1236 having the identifying characteristics of ATCC 55208 and capable of producing BMY-28960 and desxylosyl BMY-28960 upon cultivation in an aqueous medium containing an assimilable source of carbon, nitrogen, and D-serine.

DETAILED DESCRIPTION OF THE INVENTION

Figure 1:
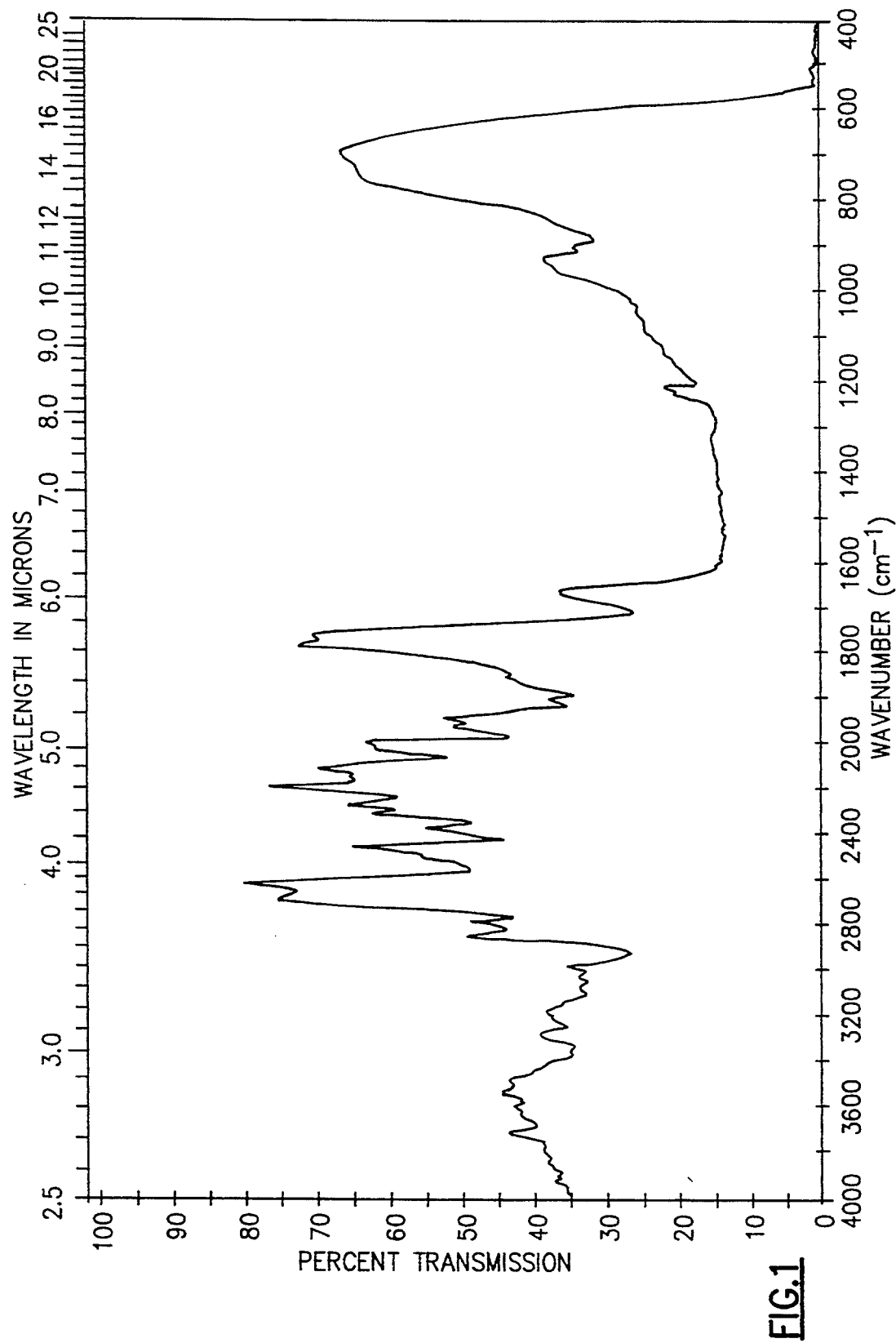
FIG. 1 is an IR spectrum (KBr) of BMY-28960.

The present invention provides a fermentation process suitable for mass production of BMY-28960 and desxylosyl BMY-28960. The process utilizes a novel microorgansim belonging to the genus Actinomadura.

I. Screening of BMY-28960-Producing Micooragnisms

A loopful of each actinomycete isolated from soil samples was inoculated as a patch onto three agar plates, namely glucose-yeast-soytone agar (glucose 1%, yeast extract 0.05%, soytone (Difco Laboratories) 0.05%, $CaCl_2.2H_2O$ 0.01% and agar 1.5%), glycerol-yeast-soytone agar (glycerol 1%, yeast extract 0.05%, soytone 0.05%, $CaCl_2.2H_2O$ 0.01% and agar 1.5%) and starch-yeast-soytone agar (soluble starch 1%, yeast extract 0.05%, soytone 0.05%, $CaCl_2.2H_2O$ 0.01% and agar 1.5%), and then incubated at 37° C. for 1 to 2 weeks. Strains that produced dark pink to dark red diffusible pigments in each agar plate were inoculated into 500-ml Erlenmeyer flasks containing 100 ml of a production medium composed of glycerol 2%, Esusan mi-to (Ajinomoto Co., Ltd.) 1.5%, $CoCl_2.6H_2O$ 0.0001%, $KH_2PO_4$ 0.1125%, $K_2HPO_4$ 0.0025% and D-serine 0.2%, and incubated with rotary shaking (200 rpm) at 32° C. After 10 days of incubation, production of BMY-28960 in the broth was monitored by the agar well assay of the supernatant using *Candida albicans* A9540 as test organism. The broths showing anti-Candida activity were centrifuged, diluted 10 fold with DMSO, and filtered (Gelman Sciences Japan, Ltd., Ekicrodisc 13CR, Pore size: 0.45 μm). The liltrates were analyzed by HPLC on Excel pak SIL-C185R (Yokogawa Electronic Co., Ltd.) using acetonitrile:0.02M phosphate buffer, pH 7.0 (15:85), at a flow rate of 1 ml/min. with 254 nm detection and by TLC on silica gel thin layer plates (Kiesel gel 60 F254 0.25 mm; mfd, Merck). The developing solvent systems used were n-butanol:acetic acid:water (2:1:1, BW-14) and methyl acetate:n-propanol:28% aq. ammonia (45:105:60, S-114). BMY-28960 has an HPLC retention time of 11.5 min. with the above solvent system and Rf values of 0.50 and 0.24 using BW-14 and S-114, respectively.

Various actinomycetes were screened and strain AB 1236 belonging to the genus Actinomadura was found to produce the desired compound at a level suitable for mass production. Taxonomical characteristics of strain AB 1236 will be described below.

II. BMY-28960-Producing Organism

Actinomadura sp. AB 1236 is a new strain isolated from a soil sample collected at Shinjuku, Tokyo, Japan on Oct. 24, 1990. A culture of strain AB 1236 has been deposited with the American Type Culture Collection under the BUDAPEST TREATY ON THE INTERNATIONAL RECOGNITION OF THE DEPOSIT OF MICROORGANISMS FOR THE PURPOSES OF PATENT PROCEDURE, and all restrictions on the availability to the public of the deposited microorganism will be irrevocably removed upon the granting of a patent from this application. The deposited culture has been assigned the accession number ATCC 55208.

A. Morphology and cultural characteristics of strain AB 1236

The media and procedures used for the taxonomic study of the strain were those described by Shirling and Gottlieb in "Methods for Characterization of Streptomyces species", *Int. J. Syst. Bact.*, 1966, 16:313–340; by Waksman in The Actinomycetes, Vol. II, "Classification, Identification and Description of Genera and Species", pp. 328–334, publ. by The Williams and Wilkins Co., Baltimore, 1961; and by Arai in *Culture Media for Actinomycetes*, publ. by The Society for Actinomycetes Japan, 1975. The strain was incubated at 37° C. for 2 to 4 weeks. Color determination was made by comparing the color of the culture with color chips according to the Manual of Color Names (Japan Color Enterprise Co., Ltd., 1987).

Strain AB 1236 grew better on organic media than on inorganic media at temperatures between 20° and 41° C. and formed a branched vegetative mycelium. The color of mature aerial mycelia was white to grayish white on both yeast starch agar and yeast-starch-malt agar (YSM, soluble starch 1%, yeast extract 0.1%, malt extract 0.1%, $CaCl_2.2H_2O$ 0.05% and agar 1.5%). Under light and scanning electron microscopes, the top of short sporophores had 2 to 8 spores per single chain. The shape of theses pores was subglobose (0.8–1.0×1.0–1.2 μm in size) and their surface was smooth. These spores were not motile. The color of vegetative mycelia and diffusible pigments on organic agar media ranged from soft pink to dark red. The color changed from soft orange to strong yellowish orange by the addition of 0.1N HCl. The cultural characteristics of strain AB 1236 on various agar media are summarized in Table 1.

TABLE 1

Cultural characteristics of strain AB 1236

| Medium | Growth | Reverse | Aerial mycelium | Soluble pigment |
|---|---|---|---|---|
| Sucrose nitrate agar (Waksman med. No. 1) | Yellowish white (393) | Yellowish white (393) | None | None |
| Glycerol nitrate agar | Grayish red (60), Good | Grayish red (60) | None | Pinkish white (391) |
| Glucose asparagine agar (Waksman med. No.2) | Yellowish white (393), Good | Yellowish white (393) | None | None |
| Yeast ext.-malt ext. agar (ISP med. No.2) | Dark red (57), Good | Dark red (57) | Grayish white (390) to pinkish white (391) | Dark red (58) |
| Oat meal agar (ISP med. No.3) | Soft pink (25), Good | Soft pink (26) | White (388), Cottony | Soft pink (26) |
| Inorganic salts-starch agar (ISP med. No. 4) | Yellowish white (393), Good | Yellowish white (393) to pinkish white (391) | None | None |
| Glycerol asparagine agar (ISP med. No. 5) | Dark red (58), Good | Dark red (58) | None | Soft pink (25) |
| Tyrosine agar (ISP med. No. 7) | Dark red (58), Good | Dark red (58) | None | Soft pink (25) |
| Nutrient agar (Waksman med. No. 14) | Yellowish white (393), Poor | Yellowish white (393) | None | None |
| Yeast starch agar | Dark grayish red (61), Good | Dark grayish red (61) | White (388) to grayish white (390), Cottony | Deep yellowish red (53) |
| Bennet's agar | Dark red (57), Good | Dark red (57) | Grayish white (390), Scant | Deep pink (22) |

B. Physiological characteristics of strain AB 1236

The physiological characteristics and the pattern of carbon source utilization of strain AB 1236 are shown in Tables 2 and 3, respectively.

TABLE 2

| Physiological characteristics of strain AB 1236 | |
|---|---|
| Test | Results |
| Starch hydrolysis (ISP med. No.4) | + |
| Nitrate reduction (Difco, nitrate broth) | − |
| 10% skimmed milk (Difco, 10% skimmed milk) | |
| Coagulation | + |

TABLE 2-continued

Physiological characteristics of strain AB 1236

| Test | Results |
| --- | --- |
| Peptonization | — |
| Cellulose decomposition (sucrose nitrate solution with a strip of paper as the sole carbon source) | — |
| Gelatin liquefaction | No growth |
| Melanine formation | — |
| On ISP med. No. 7 | |
| Temperature range for growth (°C.) | 20–41 |
| Optimum temperature (°C.) (on Yeast starch agar) | 30.5–35.5 |
| pH range for growth | 6–8 |
| Optimum pH (On trypticase soy broth, BBL) | 7 |

—: Negative
+: Positive

TABLE 3

Utilization of carbon sources by strain AB 1236

| Carbon source | Utilization |
| --- | --- |
| D-Glucose | + |
| L-Arabinose | + |
| D-Xylose | + |
| Inositol | + |
| Mannitol | + |
| D-Fructose | + |
| L-Rhamnose | + |
| Sucrose | + |
| Raffinose | + |

+: Positive
(ISP med. No. 9, 37° C for 3 weeks)

Antibiotic susceptibility of strain AB 1236 was tested using antibiotic disks (Tridisk, Eiken Chemical Co., Ltd.). The disks were placed onto the surface of yeast-glucose-malt agar (yeast extract 0.1%, glucose 1%, malt extract 0.1%, $CaCl_2.2H_2O$ 0.05% and agar 1.5%) which had been seeded by strain AB 1236 (4% inoculum), and the plates were then incubated at 37° C. for 4 days. Strain AB 1236 was resistant to 50 μg of fosfomycin and 300 U of polymixin B, and susceptible to 20 U of ampicillin, 1 μg of clavulanic acid, 2 μg of ticarcillin, 10 μg of cephalexin, 30 μg of tetracycline, 10 μg of chloramphenicol, 0.5 μg of erythromycin, 2 μg of josamycin, 2 μg of lincomycin, 5 μg of kanamycin, 5 μg of gentamicin, 5 μg of tobramycin, 2 μg of nalidixic acid, 2 μg of norfloxacin and 50 U of coilstin.

C. Chemical analysis of AB 1236 cells

Whole-cell compositions were analyzed by the method described by Becker and Lechevalier in "Rapid Differentiation between Nocardia and Streptomyces by Paper Chromatography of Whole Cell Hydrolysate", *Appl. Microb.*, 1964, 12:421–423, and in "Chemical Compositions of Cell-Wall Preparations from Strains of Various Form-Genera of Aerobic Actinomycetes", *Appl. Microb.*, 1965, 13:236–243. Strain AB 1236 contained meso-diaminopimeric acid, madurose, ribose, mannose, glucose, and galactose. Thus, strain AB 1236 has a cell wall belonging to type III B. Mycolic acids were not detected by the method of Minnikin et al in "Differentiation of Mycobacterium, Nocardia, and Related Taxa by Thin-Layer Chromatographic Analysis of Whole-Organism Methanolysates", *J. Gen. Microb.*, 1975, 88:200–204. Phospholipid analysis using the procedure of Lechevalier et al. in "Identification of Aerobic Actinomycetes of Clinical Importance", *J. Lab. Clin. Med.*, 1968, 71:934–944," and in "Chemotaxonomy of Aerobic Actinomycetes: Phospholipid Compositiony", *Biochem. Syst. Ecol.*, 1977, 5:249–260, showed that the cell wall of strain AB 1236 had a type P1 pattern containing diphosphatidylinositol mannoside, phosphatidylinositol and diphosphatidylglycerol. Analysis of the menaquinone composition using the procedure of Collins et al. in "A Note on the Separation of Natural Mixtures of Bacterial Menaquinones Using Reverse-Phase Thin-Layer Chromatography", *J. Appl. Bacteriol.*, 1980, 48:277–282, revealed 47% MK-9 (H8), 35% MK-9 (H6), 10% MK-9 (H4) and 8% MK-9 (H10). The whole-cell fatty acids determined by the method of Suzuki et al. in "Taxonomic Significance of Cellular Fatty Acid Composition in Some Coryneform Bacteria", *Int. J. Syst. Bacteriol.*, 1983, 33:188–200, consisted of 49% 14-methylpentadecanoic acid (iso 16:0), 13% 14-methylhexadecanoic acid (anteiso-17:0) and 8% 10-methylheptadecanoic acid (10Me-17:0), and other minor fatty acids.

Strain AB 1236 has morphological, cultural, and chemotaxonomic properties that are consistent with those of the genus Actinomadura Lechevalier and Lechvalier, and with the definition of this genus proposed by Kroppenstedt et al. in "Taxonomic Revision of the Actinomycete Genera Actinomadura and Microtetraspora", *System. Appl. Microbiol.*, 1990, 13:148–160. Thus, strain AB 1236 has been identified as a species of Actinomadura.

III. Antibiotic production

BMY-28960 and desxylosyl BMY-28960 may be produced by strain AB 1236 under conditions conventionally used for producing common fermentation products. The producing organism is grown in a nutrient medium containing an assimilable source of D-serine in addition to known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used.

As an assimilable source of D-serine, either D-serine or DL-serine may be used. Examples of assimilable source of carbon are glycerol; sugars such as ribose, glucose, sucrose, cellobiose; starch; and other carbohydrates such as dextran. Examples of assimilable nitrogen source are ammonium chloride, ammonium sulfate, urea, ammonium nitrate, sodium nitrate, and organic nitrogen sources such as peptone, meat extract, yeast extract, corn steep liquor, soybean powder, cotton seed flour and the like. There may also be added if necessary inorganic salts such as cobalt chloride and potassium phosphate. Furthermore, the production of antibiotic is enhanced with the addition of threonine to the production medium; threonine may be D-threonine, L-threonine or a mixture thereof. Addition of D-cycloserine thereto further improves antibiotic production. A preferred liquid medium is the one described in Example 2 or Example 3. Another more conventional liquid medium is composed of glucose and/or glycerol (1–4%), Pharmamedia (1–3%), $KH_2PO_4$ (0.1–0.2%), and D-serine (0.1–0.2%). Adekanol, silicone and the like can be used as antifoaming agents.

Production of the antibiotic may be carried out at any temperature conductive to satisfactory growth of the producing organism. Ordinarily, optimum antibiotic production is obtained in shake flasks after an incubations period of 5-14 days, although a longer period may be necessary in certain cases. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermetation tank medium. Agitation in the tank fermentor is provided by stirring and aeration may be achieved by injection of air or oxygen into the agitated mixture. Antibiotic production may be monitored using chromatographic or spectroscopic techniques, or by a conventional biological assay. Preferred fermentation conditions are aerobic cultivations at pH 5-8 at 20°-37° C. for 5-14 days, preferably at pH 6-7 at 28°-35° C. for 5-12 days.

Although the present invention describes the production of antibiotic by a specific strain of microorganism, it is widely known that the taxonomic properties of Actinomycetes may be varied naturally or artificially. Thus, it is to be understood that the process of the present invention is not limited to the particular organism mentioned, but includes variants and mutants derived from the particular strain by various artificial methods such as ultraviolet light or X-ray irradiation, or by chemical mutagenic agents such as N-methyl-N'-nitro-N-nitrosoguanidine. Mutants and variants so produced may be screened for antibiotic production by the procedure described earlier in the present disclosure.

IV. Isolation and Purification of the Antibiotic

BMY-28960 and desxylosyl BMY-28960 may be isolated from cultured broths by conventional procedures for isolating hydrophilic acidic substances. Examples of such procedures include organic solvent extraction, ion exchange resin, partition chromatography, and acidic precipitation; these may be used either alone or in combination. An illustrative isolation and purification procedure follows. After completion of the fermentation, the broth is adjusted to pH 2.0 and centrifuged or filtered. The resulting supernatant or filtrate is adsorbed on high porous polymer resin such as Diaion HP-20 (Mitsubishi Kasei Co.) and eluted with water miscible organic solvents such as methanol or acetone. The eluate thus obtained is concentrated and lyophilized to yield a crude antibiotic complex. For further purification, the crude material may be applied to a reversed phase silica gel column such as YMC-ODS A60 (Yamamura Chemical Lab.) and eluted with acetonitrile:0.02M phosphate buffer, pH 7.0. Fractions containing BMY-28960 are pooled and desalted to provide pure BMY-28960. Desxylosyl BMY-28960 may be obtained by a similar isolating and purification procedure; preferably, the fermentation broth is not acidified.

V. Physico-chemical Properties of the Antibiotic

BMY-28960 obtained by the process of this invention has the following physico-chemical properties which are identical with those of BMY-28960 obtained by semisynthesis as disclosed in EP 432,527.

Figure 2:
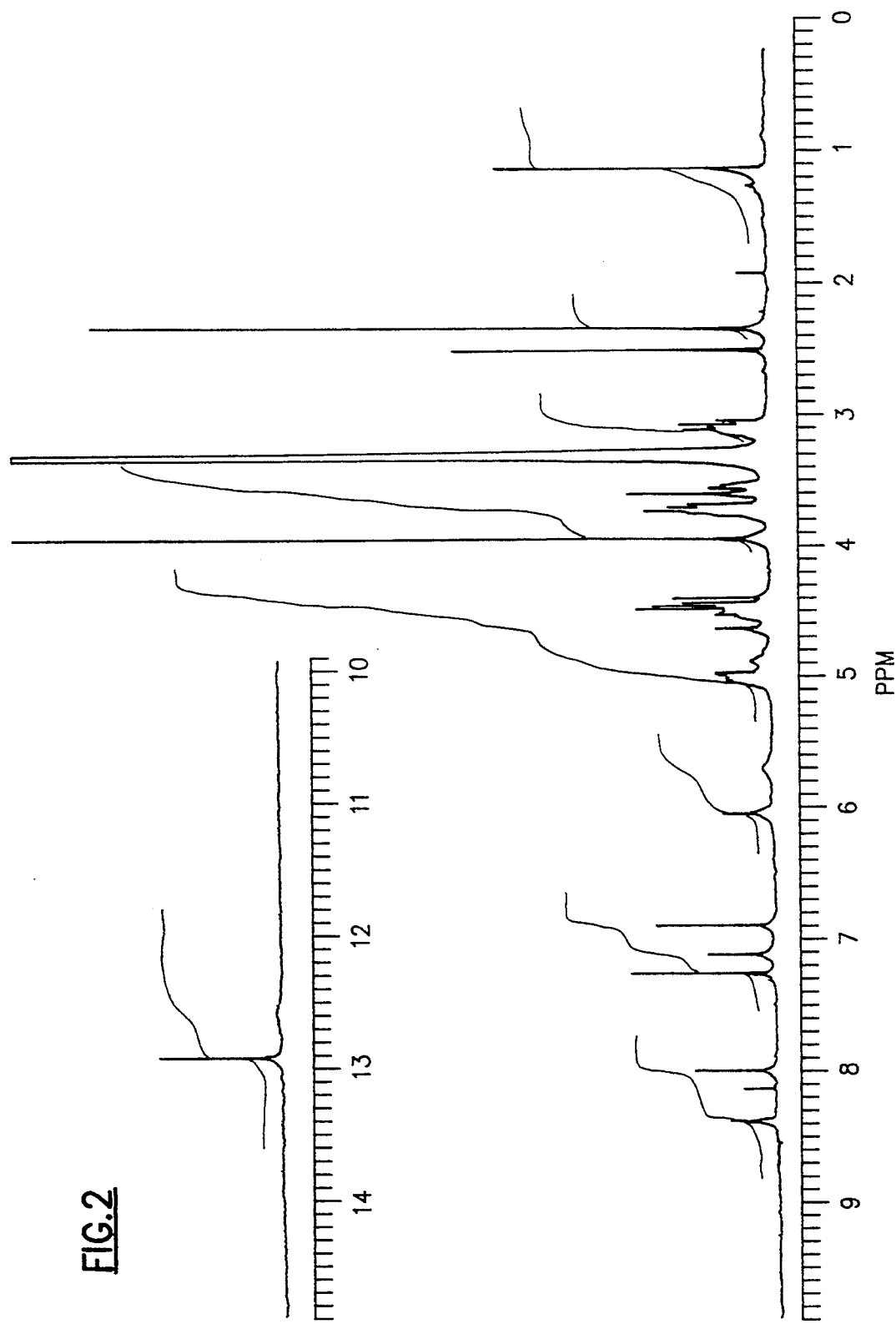
FIG. 2 is a $^1$H NMR spectrum (DMSO-$d_6$, 400 MHz) of BMY-28960.
Figure 3:
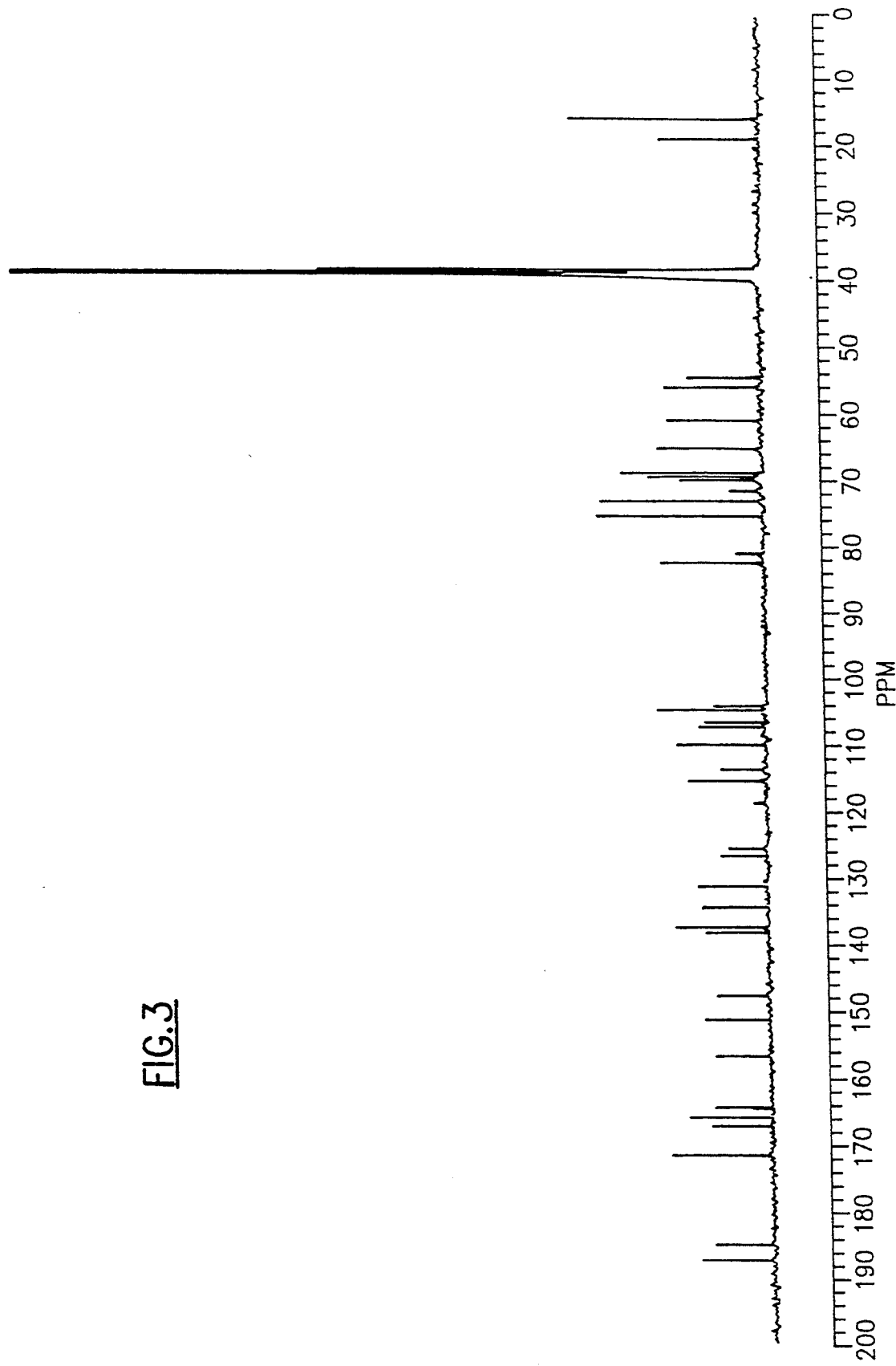
FIG. 3 is a $^{13}$C NMR spectrum (DMSO-$d_6$, 100 MHz) of BMY-28960.

(1) Appearance: Amorphous deep reddish orange powder
(2) Melting point: >220° C. (grad. dec.)
(3) FAB-MS (positive): m/z 844(M+H)+
(4) Molecular formula: $C_{39}H_{41}NO_{20}$
(5) UV absorption spectrum, λmax nm(ε): 0.02N NaOH:MeOH(1:1): 211(34,700), 320(15,100), 498(14,100)
(6) IR spectrum: as shown in FIG. 1
(7) Solubility in solvent
  Soluble: Dimethyl sulfoxide, N,N-dimethyl-formamide and alkaline water
  Slightly soluble: Ethanol, methanol and acetone
  Isoluble: Ethyl acetate, benzene, chloroform, acidic water, etc.
(8) Thin layer chromatography (Silica gel plate): Rf=0.24 (methyl acetate:n-propanol:28% agueous ammonia=45:105:60)
(9) HPLC analysis
  Column: Cosmosil 5C$_{18}$-AR, 5 μm, 4.6 mm I.D.×150 mm
  Eluent: CH$_3$CN:0.02M phosphate buffer, pH 7.0 (15:85)
  Flow rate: 1.0 ml/min.
  UV detector: 254 nm
  Retention time: 11.5 min.
  Internal standard: Pradimicin A (Rt=9.7 min.)
(10) $^1$H NMR spectrum:as shown in FIG. 2
(11) $^{13}$C NMR spectrum:as shown in FIG. 3

Figure 4:
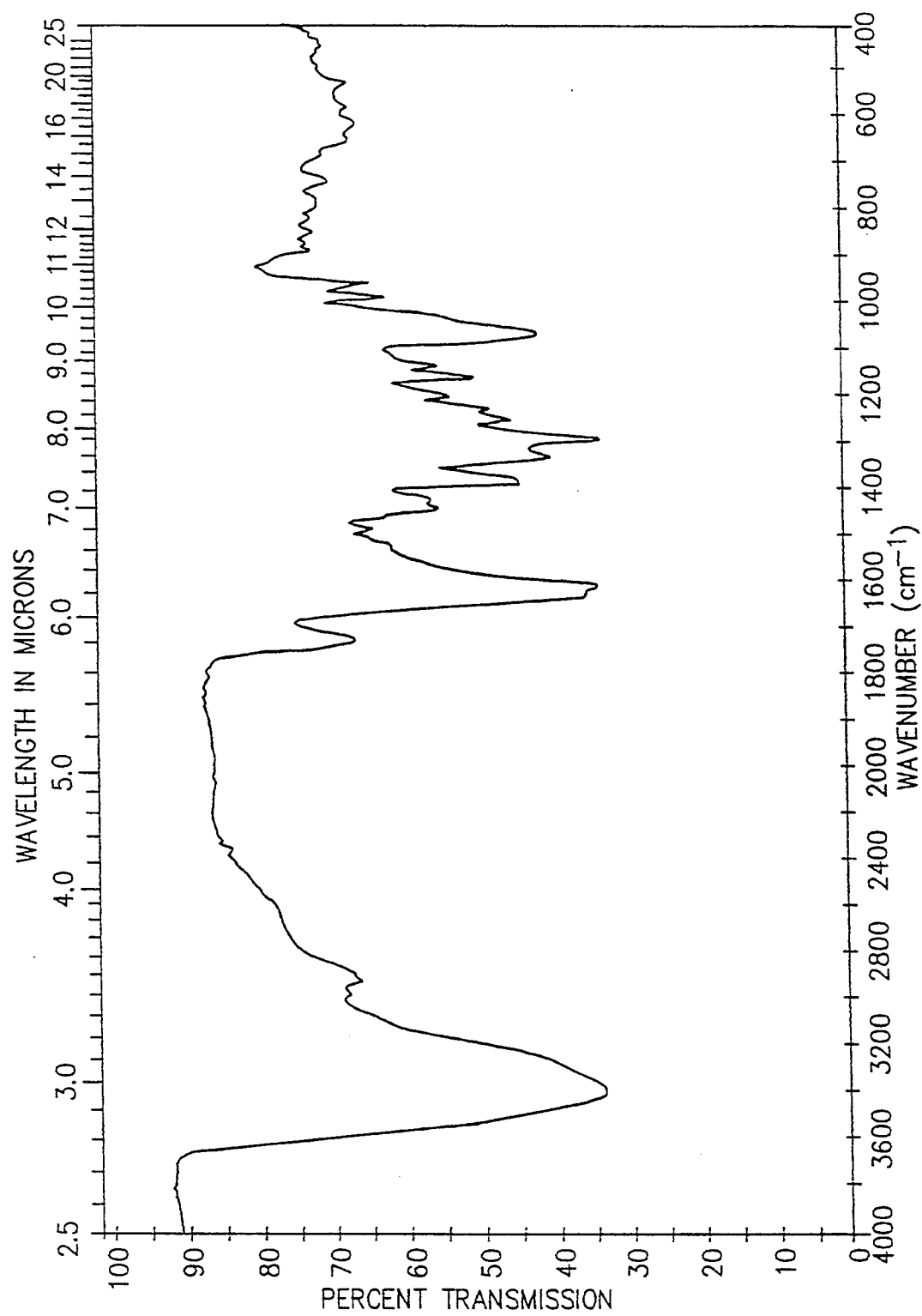
FIG. 4 is an IR spectrum (KBr) of desxylosyl BMY-28960.
Figure 5:
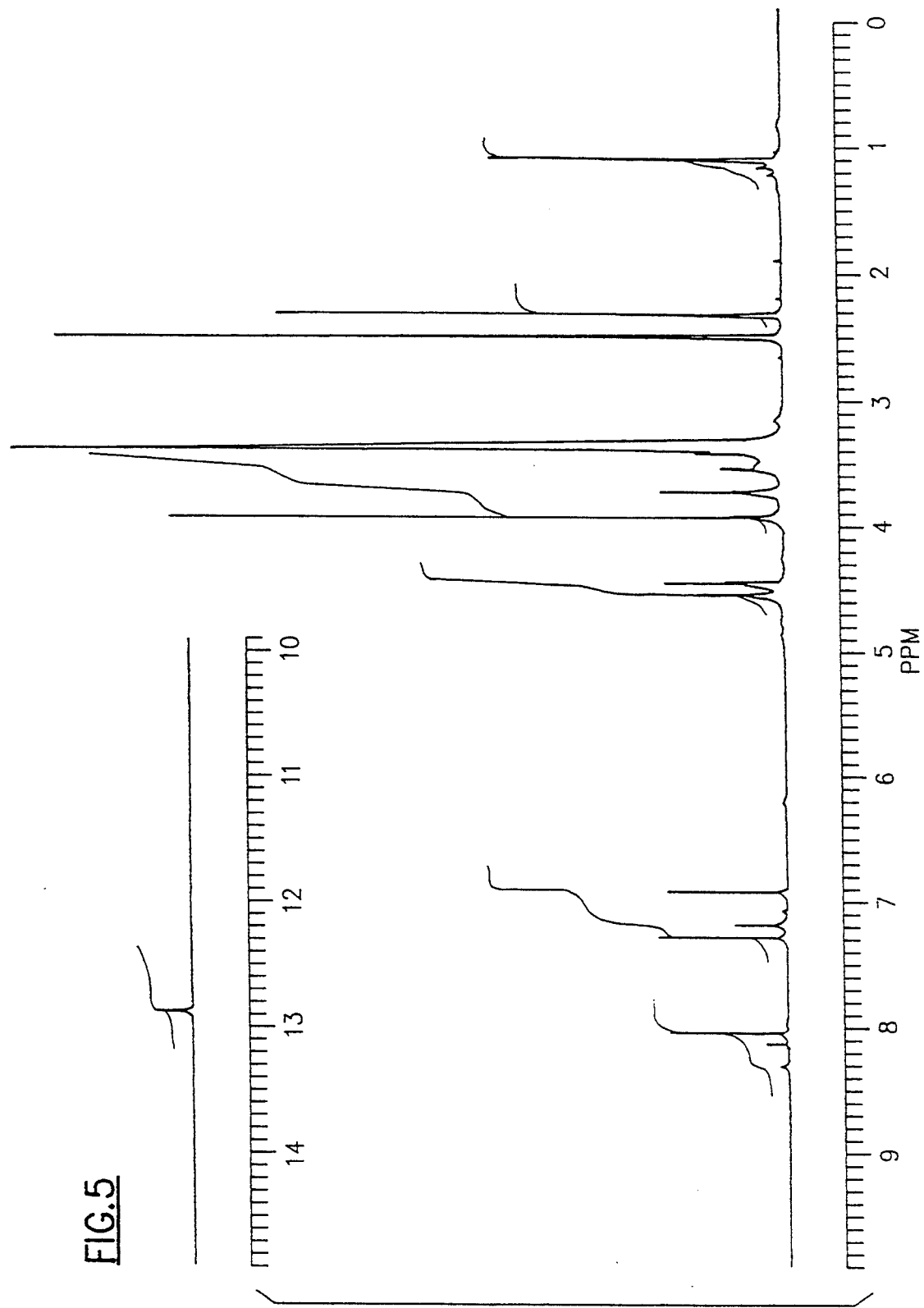
FIG. 5 is a $^1$H NMR spectrum (DMSO-$d_6$, 400 MHz) of desxylosyl BMY-28960.

Desxylosyl BMY-28960 has the following physico-chemical properties:

(1) Appearance: Deep reddish orange powder
(2) Melting point: >180° C.
(3) HR-FAB-MS (positive): m/z 712.1871 (M+H)+
(4) Molecular formula: $C_{34}H_{33}NO_{16}$
(5) UV absorption spectrum, λmax nm(ε): in H$_2$O—MeOH-DMSO (4.5:4.5:1): 470(10,100), in 0.02N HCl—MeOH,DMSO (4.5:4.5:1): 461 (10,600) in 0.02N NaOH-MeOH (1:1): 213(31,500), 242(30,100), 498(12,600)
(6) IR spectrum (KBr) $\nu_{max}cm^{-1}$: as shown in FIG. 4
(7) Solubility in solvent
  Soluble: Dimethyl sulfoxide, dimethylformamide, and alkaline water
  Slightly soluble: Ethanol, methanol, acetone and acetonitrile
  Isoluble: Acidic water, n-butanol, ethyl acetate, chloroform, and other common organic solvents
(8) $^1$H NMR spectrum: as shown in FIG. 5.

VI. Biological Activities of the Antibiotic

The in vitro antifungal activities of BMY-28960 and desxylosyl BMY-28960 obtained by the present fermentation process were determined by a conventional agar dilution method on yeast morphology agar containing 1/15M phosphate buffer (pH 7.0). The results are shown in Tables 4 and 5.

TABLE 4

| In vitro antifungal activity of BMY-28960 | | | |
|---|---|---|---|
| Test organism | BMY-28960 | Amphotericin B | Ketoconazole |
| Saccharomyces cerevisiae ATTC 9763 | 3.1 | 0.4 | 100 |
| Candida albicans A9540 | 6.3 | 0.4 | 25 |
| Candida albicans ATCC 38247 | 1.6 | 6.3 | 6.3 |
| Candida albicans ATCC 32354 (B311) | 3.1 | 0.2 | 50 |
| Candida albicans 83-2-14 (Juntendo) | 12.5 | 0.4 | 25 |
| Candida tropicalis 85-8 (Kitasato) | 12.5 | 0.4 | 100 |
| Candida tropicalis IFO 10241 | 3.1 | 0.4 | 50 |
| Cryptococcus neoformans D49 | 3.1 | 0.4 | 6.3 |
| Cryptococcus neoformans IAM 4514 | 6.3 | 0.4 | 6.3 |
| Aspergillus fumigatus IAM 2034 | 6.3 | 0.4 | 3.1 |

TABLE 4-continued

In vitro antifungal activity of BMY-28960

| Test organism | BMY-28960 | Amphotericin B | Ketoconazole |
|---|---|---|---|
| Trichophyton mentagrophytes #4329 | 6.3 | 0.4 | 0.8 |

Medium: Yeast morphology agar + 1/15M phosphate buffer (pH 7.0)
Inoculum size: $10^6$ cells/ml ($10^7$ cells/ml for T. mentagrophytes)
Incubation conditions: 28° C., 40 hrs. (60 hrs. for T. mentagrophytes)

TABLE 5

In vitro antifungal activity of desxylosyl BMY-28960

| Test organism | Desxylosyl BMY-28960 | BMY-28960 | Amphotericin B |
|---|---|---|---|
| Saccharomyces cerevisiae ATCC 9763 | 3.1 | 1.6 | 0.8 |
| Candida albicans A9540 | 3.1 | 3.1 | 0.8 |
| Candida albicans IAM 4888 | 3.1 | 3.1 | 0.8 |
| Candida albicans ATCC 32354 (B311) | 3.1 | 3.1 | 0.8 |
| Candida albicans 83-2-14 (Juntendo) | 1.6 | 3.1 | 0.8 |
| Candida tropicalis 85-8 (Kitasato) | 1.6 | 12.5 | 1.6 |
| Candida tropicalis IFO 10241 | 6.3 | 12.5 | 1.6 |
| Cryptococcus neoformans D49 | 1.6 | 3.1 | 0.8 |
| Cryptococcus sp. IAM 4514 | 3.1 | 1.6 | 0.8 |
| Aspergillus fumigatus IAM 2034 | 6.3 | 3.1 | 0.8 |
| Trichophyton mentagrophytes #4329 | 6.3 | 3.1 | 1.6 |

Medium: Yeast morphology agar + 1/15M phosphate buffer (pH 7.0)
Incolum size: $10^6$ cells/ml (Tm: $10^7$ cells/ml)
Incubation conditions: 28° C., 40 hrs. (60 hrs. for T. mentagrophytes)

The in vivo efficacy of BMY-28960 was evaluated against Candida albicans A9540 systemic infection in male ICR mice (20–24 g body weight). Five mice are used for each dose level. Mice were challenged intravenously with 10 times the median lethal dose of the pathogen suspended in saline and BMY-28960 was intravenously administered once immediately after the challenge. The median protective dose ($PD_{50}$) was calculated from survival rates recorded on day 21. The results are summarized in Table 6.

TABLE 6

In vivo efficacy against C. albicans A9540 systemic infection in mice

| Compound | $PD_{50}$ (mg/kg, i.v.) |
|---|---|
| BMY-28960 | 6.7 |
| Pradimicin A | 10 |
| Amphotericin B | 0.31 |
| Fluconazole | >50 |

BMY-28960 was well-tolerated in ICR mice; neither lethality nor apparent side effects were noted following intravenous administration of BMY-28960 up to 600 mg/kg The following examples are provided in order to more fully illustrate the present invention, and they shall not be construed as in any manner limiting the scope of the invention.

EXAMPLE 1

Seed culture

A stock culture of the producing organism, Actinomadura sp. AB 1236, (ATCC 55208) was streaked on YSM agar slant and incubated at 37° C. for 2 weeks. One loopful of the strain was inoculated into a 500-ml Erlenmeyer flask containing 100 ml of a medium composed of glucose 0.5%, soluble starch 2%, yeast extract 0.2%, NZ-case 0.3%, fish meal extract D30X (Banyu Eiyou K.K.) 0.5% and $CaCO_3$ 0.3% (the pH of the medium was adjusted to 7.0 before autoclaving). The culture was incubated on a rotary shaker at 32° C. for 5 days and was used as the seed culture.

EXAMPLE 2

Flask fermentation

Each 5-ml portion of the seed culture as set forth in Example 1 was transferred into a 500-ml Erlenmeyer flask containing 100 ml of production medium composed of glycerol 2%, Esusan mi-to (soybean meal; Ajinomoto Co., Inc.) 1.5%, $K_2HPO_4$ 0.0025%, $KH_2PO_4$ 0.1125%, $CoCl_2.6H_2O$ 0.0005% and D-serine 0.125% with D-cycloserine (Wako Pure Chemical Industries Ltd.) 10 μg/ml. The culture was incubated on a rotary shaker operating at 200 rpm and 28° C. for 12 days, at which time production of BMY-28960 reached 530 μg/ml.

EXAMPLE 3

Flask fermentation (effect of added threonine)

Each 5-ml. portion of the seed culture as set forth in Example 1 was transferred into a 500-ml Erlenmeyer flask containing 100 ml of production medium composed of glycerol 2%, Pharmamedia (Traders Protein) 1.5%, $KH_2PO_4$ 0.1%, L- or D-threonine 0.2%, $CoCl_2$ $6H_2O$ 0.0005%, D-serine 0.2% and D-cycloserine 10 μg/mi. The culture was incubated on a rotary shaker operating at 200 rpm for 11 days at 28° C. To see the effect of threonine one the production of BMY-28960, fermentation was also carried out in the absence of threonine. The results are summarized below:

| Amino acid | Production of BMY-28960 |
|---|---|
| L-Threonine | 1008 μg/ml |
| D-Threonine | 954 |
| — | 780 |

EXAMPLE 4

Isolation and purification of BMY-28960

The fermentation broth (2.0 liter) of Example 2 was acidified to pH 2.0 using 6N HCl and centrifuged. The supernatant (1.7 liter) was applied on a column of Diaion HP-20 (300 ml), and the column was first washed with water (1.5 liter) and then eluted with 1.6 liter of methanol. The eluate was concentrated and then lyophilized to yield 2.1 g of a crude solid. This solid was dissolved in 1 liter of water, and the pH of the solution was adjusted to 6.3 with 1N NaOH. The solution was applied on a column of Diaion HP-20, and the column was first washed with a mixture of 0.002N HCl:acetone (1:1) and then eluted with 1 liter of a mixture of 0.002N NaOH:acetone (1:1). Concentration of the eluate afforded a solid (690 mg). A part (400 mg) of the solid was dissolved in acetonitrile:0.02M phosphate buffer, pH 7.0 (12.5: 87.5, 30 ml) and subjected to chromatography on a column of YMC gel, ODS A60 (500 ml, Yamamura Chemical Lab.) which had been equilibrated with the same solvent system. Elution was done with the same solvent. The fractions containing BMY-28960 were concentrated, desalted by Diaion HP-20 and lyophilized to give BMY-28960 (82 mg).

EXAMPLE 5

Isolation and purification of desxylosyl BMY-28960

The culture broth (25 L) prepared by fermentation of strain AB1236 in the presence of D-serine was centrifuged. The supernatant (27 L) was passed through 3.8L of Diaion HP-20. The resin was washed successively with 80% aq. acetone (8 L) and acetone-0.01N HCl (60:40) mixture (12 L), and then eluted with acetone-0.01N NaOH (60:40) mixture (12 L) to yield 16.04 g of crude. The complex (2 g) was dissolved in 200 ml of a mixture of $CH_3CN$-0.02M phosphate buffer, pH 7.0 (13:87) and charged on a column of YMC gel, ODS-A60 (10 L, Yamamura Chemical Lab.) which had been equilibrated with the same solvent system. Elution was carried out with the solvent system used to dissolve the sample and the eluates were monitored by HPLC (Column:Cosmosil $5C_{18}$-AR, 5 μm, 4.6 mm i.d.×150 mm, Nacalai Tesque Inc., Mobile phase: $CH_3CN$-1/15 M phosphate buffer, pH 3.5 (27:73), Flow rate: 1.0 ml/min., Detection:UV absorption at 254 nm, Retention time: desxylosyl BMY-28960 8.3 min.: BMY-28960, 7.6 min.). The faster eluted red fraction (3.7 L) containing desxylosyl BMY-28960 was concentrated, and chromatographed on a column of Diaion HP-20 (30 ml) using acetone- 0.1N NaOH (60:40) mixture (50 ml) as eluent. The red eluates were concentrated and lyophilized to afford 29 mg of solid. An aqueous solution (30 ml) of the sample was adjusted to pH 2.5 with 0.1N HCl to deposit pure desxylosyl BMY-28960 (19 mg). The slower eluted fraction (24 L) from YMC gel chromatography was similarly worked up to afford 700 mg of pure BMY-28960.

We claim:

1. A biologically pure culture of the microorganism Actinomadura sp. AB1236 (ATCC 55208) and mutants thereof.

* * * * *